(12) United States Patent
Ebert et al.

(10) Patent No.: US 8,554,902 B2
(45) Date of Patent: Oct. 8, 2013

(54) SYSTEM AND METHOD FOR REMOTELY MAINTAINING DEVICES

(75) Inventors: Rüdiger Ebert, Adelsdorf (DE); Axel Fischer, Wermsddorf (DE)

(73) Assignee: Siemens Aktiengesellschaft, München (DE)

( * ) Notice: Subject to any disclaimer, the term of this patent is extended or adjusted under 35 U.S.C. 154(b) by 1802 days.

(21) Appl. No.: 11/228,147

(22) Filed: Sep. 16, 2005

(65) Prior Publication Data

US 2006/0064491 A1    Mar. 23, 2006

(30) Foreign Application Priority Data

Sep. 21, 2004 (DE) .......................... 10 2004 045 743

(51) Int. Cl.
*G06F 15/173* (2006.01)
(52) U.S. Cl.
USPC ........... 709/224; 709/225; 709/226; 709/217; 709/218; 709/219
(58) Field of Classification Search
USPC .......... 709/217–219, 223–226; 700/108–110, 700/174
See application file for complete search history.

(56) References Cited

U.S. PATENT DOCUMENTS

| | | | | |
|---|---|---|---|---|
| 5,099,424 A | * | 3/1992 | Schneiderman | 705/3 |
| 5,592,620 A | * | 1/1997 | Chen et al. | 709/223 |
| 5,805,776 A | * | 9/1998 | Juengst et al. | 706/59 |
| 5,949,976 A | * | 9/1999 | Chappelle | 709/224 |
| 6,325,540 B1 | * | 12/2001 | Lounsberry et al. | 378/207 |
| 6,446,123 B1 | * | 9/2002 | Ballantine et al. | 709/224 |
| 6,621,413 B1 | * | 9/2003 | Roman et al. | 340/539.12 |
| 6,684,242 B1 | * | 1/2004 | Bahlmann | 709/222 |
| 6,856,257 B1 | * | 2/2005 | Van Heteren | 340/870.03 |
| 6,957,128 B1 | * | 10/2005 | Ito et al. | 701/1 |
| 2002/0007237 A1 | * | 1/2002 | Phung et al. | 701/33 |
| 2002/0057456 A1 | * | 5/2002 | Dauer et al. | 358/1.15 |
| 2003/0014505 A1 | * | 1/2003 | Ramberg et al. | 709/223 |
| 2003/0037132 A1 | * | 2/2003 | Abdollahi et al. | 709/223 |
| 2003/0135382 A1 | * | 7/2003 | Marejka et al. | 705/1 |
| 2004/0133672 A1 | * | 7/2004 | Bhattacharya et al. | 709/224 |
| 2005/0249169 A1 | * | 11/2005 | Fong | 370/338 |

FOREIGN PATENT DOCUMENTS

| | | |
|---|---|---|
| DE | 100 57 625 | 5/2001 |
| WO | WO 00/00840 | 1/2000 |

* cited by examiner

*Primary Examiner* — Ian N Moore
*Assistant Examiner* — Dung B Huynh
(74) *Attorney, Agent, or Firm* — Lempia Summerfield Katz LLC

(57) ABSTRACT

A method for maintaining a device via a remote service computer initiates a transmission of maintenance data via the device or the service computer, transmits maintenance data from the device to the service computer, and evaluates the maintenance data received from the device using the service computer. The method further transmits at least one monitoring parameter request from the service computer to the device as a function of the evaluation of the maintenance data, and at least one parameter value of the at least one requested monitoring parameter from the device to the service computer, then evaluates the at least one monitoring parameter value; and displays the evaluation of the at least one monitoring parameter value via a display device of the service computer.

31 Claims, 3 Drawing Sheets

SYSTEM AND METHOD FOR REMOTELY MAINTAINING DEVICES

FIELD

The present embodiments relate, in general, to maintenance systems and, more particularly, to a system and method for maintaining a device via a remote service computer.

BACKGROUND

Remote maintenance of technical devices, for example in the fields of medicine, industry or also in private households, has become increasingly important. For example, in medical technology, image-producing devices, for example X-ray devices, computer-tomography devices (CT devices), magnetic resonance devices (MR devices), or ultrasound devices, and radiological or clinical information systems, such as (radiology information systems (RIS) or hospital information systems (HIS), are generally operated within a framework of a first maintenance level by technical service personnel assigned to a hospital. The personnel, at the occurrence or use of more targeted or complex problems, make use of the assistance of manufacturers or special service providers via remote maintenance within the framework of higher maintenance levels. Similar maintenance level scenarios are to be found in working areas with a multitude of computer-assisted workstations, in chemical or analytical industrial laboratories with laboratory devices, or in the industrial field in connection with complex processing installations or sequence controls. A multitude of potential technical problems can be related to comparatively simple-to-identify reasons, and can often be repaired comparatively simply. Such problems, for example connecting cables not inserted, lack of printing ink, etc., can mostly be remedied at the site without special knowledge of the devices, by obtaining consumable materials as needed. An identification of more complex problems can also often be provided by unspecialized service technicians at the site, such as where a test routine may be run to exclude potential, but irrelevant, causes of a problem, or for tracing an actual cause.

A system for the remote maintenance of an MR device is known from WO 00/00840, wherein a monitoring parameter is checked via a sensor. The monitoring parameter is a sensor which monitors a function of a cooling system for cooling superconducting MR magnets. Since the magnets constitute a substantial portion of the costs of an MR device, damages from undetected errors in the cooling system may be prevented. Therefore, the values of the monitoring parameters are continuously evaluated and, in case of an erroneous function, a warning message is issued via a telephone modem or a telephone modem cascade. In addition, the monitoring parameter can also be detected via dialing a telephone through the telephone modem, so that a service technician can regularly check the functioning of the cooling system.

A system is known from U.S. Pat. No. 6,621,413, wherein an MR device is also remotely monitored. One or several monitoring parameters of the MR device are continuously detected and automatically evaluated. If the evaluation points to a problem, an error report is deposited in or communicated to a service center. Further, the device which is mobile can be checked or interrogated regarding position information. Moreover, a display of device settings, software updates or telephone numbers is possible or a report is sent in case of problems.

Thus, these known systems allow remote maintenance in such a way that parameter values are collected in the form of monitoring parameters by appropriate sensors and are remotely transmitted. However, for performing checks directly at the device, for example processing of error search tree structures for localizing a problem, the service technician performs prescribed checking acts directly at the device in accordance with service documentation. In accordance with the service documentation, he performs instructions provided by the error search tree structure and makes checks, which lead to the identification of a problem cause through the branches of the search tree structure.

BRIEF SUMMARY

The present invention is defined by the appended claims. This description summarizes some aspects of the present embodiments and should not be used to limit the claims.

A first check of a device by remote control is sought. A method comprises the acts of:

d) remotely transmitting at least one parameter request from a service computer to the device as a function of an evaluation of the maintenance data, e) remotely transmitting at least one parameter value of at least one monitoring parameter determined by the monitoring parameter request from the device to the service computer as a function of the receipt of the monitoring parameter request, f) evaluating the at least one monitoring parameter received from the device by the service computer, and g) displaying the evaluation via a display device of the service computer as a function of the result of the evaluation of the at least one received monitoring parameter value.

Via the interaction between the service computer and the device to be serviced, monitoring predefined monitoring parameters and making inquiries regarding determined monitoring parameters matched or corresponding to certain situations is possible. As such, a remote check may not be limited to the evaluation of preset monitoring parameter sets or constellations, but may enable inquiries or investigations regarding determined parameters when operating a check routine, for example an error search tree structure. Thus, for example, loading the service documentation into the service computer may be useful, so that the knowledge regarding the respective checking routine is available at the service computer. Based on this service documentation, an inquiry regarding the parameter values for a determined checking routine may be performed. Moreover, these monitoring parameter values are automatically evaluated by the service computer to determine which branch of an error search tree structure should be followed and which monitoring parameter should be analyzed or interrogated next in accordance with this branching. Error search tree structures may also be interactively processed remotely without a service technician becoming directly active at the site of the device to be serviced and without having to make entries in the service computer. From the interactive processing of the check routine, the service computer can show via the display device whether any and which acts are to be performed at the device to be serviced. As such, the service technician automatically receives a first check outcome, via which he can decide whether a maintenance act is to be performed directly at the site, and if needed, whether he can enter such a maintenance act in his work schedule in order to be able to coordinate optimally his different maintenance activities.

A web pad, for example, can be used as the service computer, which is connected via a wireless local area network (WLAN) with the respective work environment, for example a hospital data network. The web pad is configured via appropriate service software, as well as service documentation to automatically taking up communications with the device to be serviced, provided the latter is also linked with the WLAN. Via the automatic remote checking of the device, the service technician can accelerate maintenance acts, which may need predetermined consumable materials or tools, because the service technician can obtain and bring these with him from the start without needing prior storage at or near the device. Moreover, the automatic processing of test routines by the service computer provides that the service technician himself need not operate the service software. As such, even service technicians who are not trained can perform an initial check via the service software, for example within the framework of a first service level to be performed by the user of the respective device himself, without needing any training in the handling of the service software.

In an advantageous aspect, a further monitoring parameter request is remotely transmitted by the service computer to the device as a function of the evaluation of the at least one monitoring parameter received by the device. As such, not only a simple branching of an error search tree structure can be processed, but that also several resulting branchings can be sequentially processed.

In a further advantageous aspect, the remote transmission of the maintenance data is initiated by the service computer based on an input by the operator into the service computer. As such, the service technician or the user can trigger the automatic interactive checking from afar or remotely at a time selected by himself. The service technician who has to service several devices can, for example, start the remote check immediately prior to selecting the next device in order to be able to plan maintenance acts at appropriate times. When reaching the device or, if appropriate prior to reaching the device, the service technician may cancel a visit or maintenance of the device not requiring maintenance from his work schedule.

In a further advantageous aspect, the service data transmitted from the device includes a device identification characteristic for the respective device. As such, the device to be serviced can be individually identified in a data network to which several devices have been linked. Moreover, the device identification can also provide information as to which type of device exists in what version and in what configuration. This knowledge is useful for future planning of maintenance acts, as well as for the activation of the service software which is relevant to the respective device.

In a further advantageous aspect, the maintenance data transmitted from the device comprises a status recognition which is characteristic of an operational state of the device.

In this arrangement, the operational state of the device can show, for example, whether the device is in use at that moment or is available for performing maintenance acts. Moreover, the operational state can also include information as to whether the device is being operated in an error-caused emergency mode, so that maintenance acts are urgently needed, or whether the device is in an operational state which would permit a maintenance act only at the end of a determined period of time, for example a cooling phase.

In a further advantageous aspect, the indication of the outcome of the evaluation takes place via an acoustic indicator device.

The acoustic device offers the option that a mobile service technician, who for example is busy with a device or can be en route in an automobile, for which reason he cannot keep an optical indicator permanently or temporarily in view, can yet be advised of the outcome of a remote check of a device.

In a further advantageous aspect, the indicator comprises the generation of an indicator sound as a function of the urgency of a maintenance act appropriate for the device. As such, in connection with acute interference cases or substantially urgent maintenance acts, the attention of the service technician can be captured or focused relatively quickly via a tailored indicator sound.

In a further advantageous aspect, the display of the evaluation outcome may contain information regarding the position of the device. As such, the service technician can optimally include a maintenance act at the device in his work schedule in that, for example, he sequentially visits several, locally adjoining devices, or in that he can immediately visit devices, in whose vicinity he happens to be.

In a further advantageous aspect, the display of the evaluation outcome contains information regarding tools or consumable materials for a maintenance act pending for the device, and/or information regarding operating acts and device settings in respect to a maintenance act pending in connection with the device. This arrangement offers the option to the service technician of procuring special tools or consumable materials, or to inform himself regarding special operating acts and device settings prior to visiting the device to be serviced. This arrangement provides the service technician with an opportunity to procure tailored tools or consumable materials, or to be informed about predetermined operating acts and device settings prior to visiting the device to be serviced. As such, a situation can be avoided in which service technician is forced to determine at the site what is needed, because of which an already started maintenance act may be interrupted in order to procure the tools or consumable materials.

A maintenance module is configured so as to determine a monitoring parameter received as a product or outcome of a monitoring parameter request, which can be contained in the data received by the remote transmission module at the service computer, to determine a sensor assigned to the monitoring parameter as a function of this transmitted monitoring parameter, and to receive monitoring parameter values from the determined sensor. The maintenance module can remotely transmit the parameter values through the remote transmission module at the device.

In the above described method, an apparatus system offers the advantage that check routines which, for example, contain the processing of error search tree structures, can be performed remotely and in an automated manner. The structure of the system at the location of the service computer permits the realization via the employment of a WLAN, LAN, WAN or other network to which end the respective remote transmission modules as network interfaces. Moreover, the maintenance module can be integrated into a web pad, which can be transported and operated in a relatively simple and inexpensive way by a mobile service technician.

In an advantageous aspect of the apparatus system, the remote maintenance module is configured to automatically evaluate at least one monitoring parameter value transmitted from the remote transmission modules at the device, to determine a further monitoring parameter which is different from the outcome of this evaluation, and to remotely transmit a monitoring parameter request regarding the further monitoring parameter via the remote transmission module at the service computer. As such, not only individual branching of an error search tree structure can be processed, but also several subsequent branching.

Illustrative exemplary embodiments of the invention are described in further detail below with reference to, and in conjunction with, with the figures.

BRIEF DESCRIPTION OF A VIEW OF THE DRAWING

DETAILED DESCRIPTION

Figure 1:
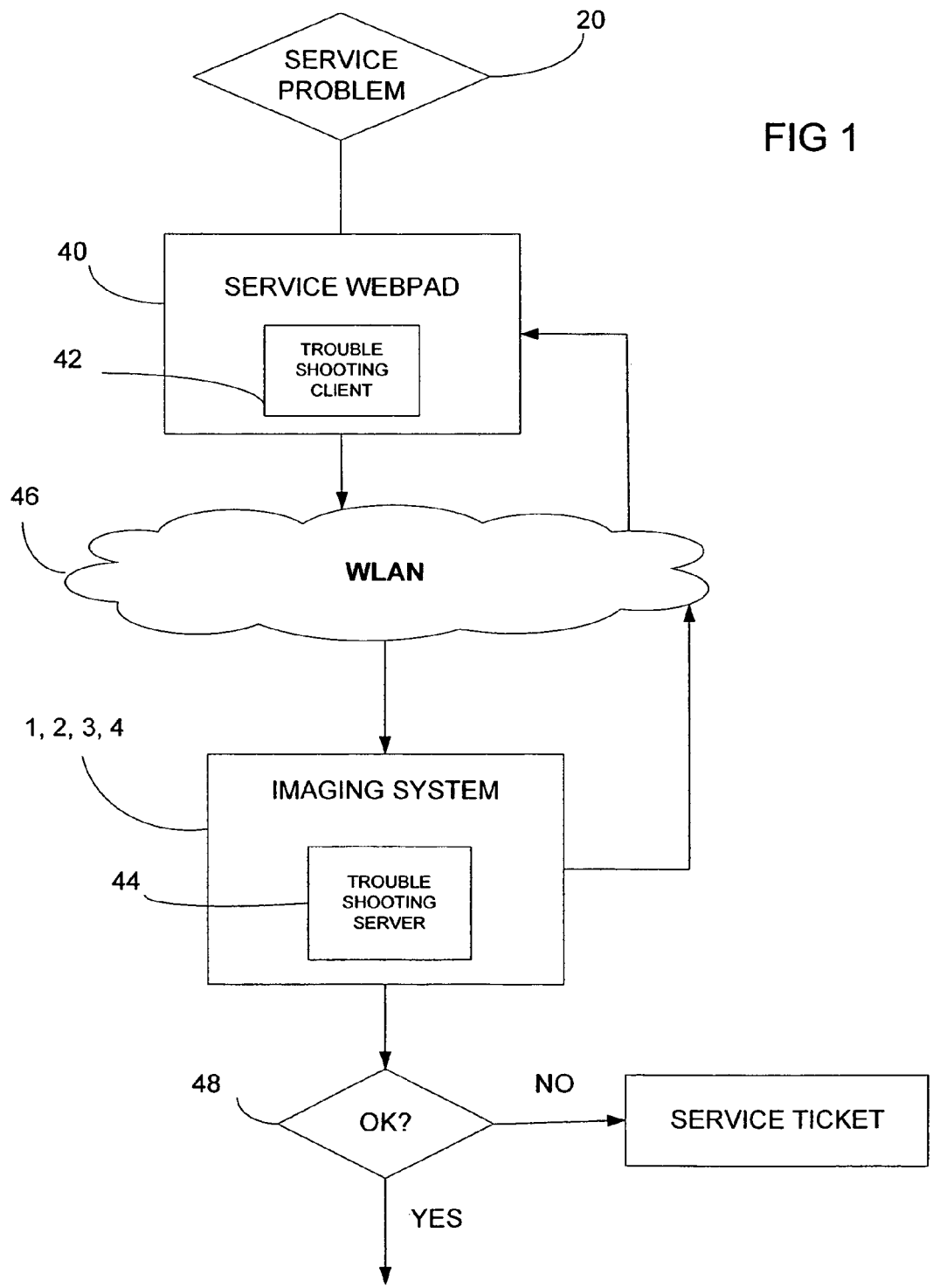
FIG. 1 is a schematic diagram of one embodiment of the apparatus system.

A procedure or progression of a servicing or maintenance act is schematically represented in FIG. 1. A maintenance problem at the start of the servicing progression initiates the proposed method or process. The maintenance problem can be a request from a service technician made via the service computer. For example, the service technician can check, test or interrogate the next device listed in his work schedule or, because of a customer query due to a technical interference or a technical problem, he can check the device which is the subject of the customer query. However, the progression can also be initiated by the device in that, for example, the device transmits a status report to the service computer, which is regularly generated after a determined number of operating hours or, in case of the appearance of a technical problem or interference, the device transmits an appropriate interference report to the service computer.

After the progression has been started, the service computer becomes active in the form of a trouble-shooting client. The service computer is a web pad 40, which for a service technician is relatively simple to operate, easy to transport and is substantially sufficient for mobile use by having a functional size. Service software is recorded on the web pad 40 to functionality of a trouble-shooting client 42 is implemented. Service documentation is furthermore recorded on the web pad 40. The service documentation contains information regarding device settings, maintenance acts and consumable materials for devices to be maintained in various possible device configurations. The service documentation provides initial values to the trouble-shooting client 42, on the basis of which the trouble-shooting client 42 can initiate and control a remote request. It furthermore provides the service technician with information for implementing or planning maintenance acts. Other devices than the web pat 40 may be used, such as a computer or server.

The trouble-shooting client 42 checks or interrogates the device to be maintained, such as one or more imaging systems 1, 2, 3, and/or 4, via a wireless local area network (WLAN) or other computer network.

A trouble-shooting server 44 (e.g., network server, imaging system processor, computer or database manager) is connected with the imaging system 1, 2, 3, 4, which implements the functionality of the device for the remote request. The trouble-shooting server 44 monitors individual parameters of the imaging system 1, 2, 3, 4, stores information regarding the operational state of the latter, and furthermore makes information available which unequivocally or equivocally characterizes the imaging system 1, 2, 3, 4, and the device configuration for the purpose of maintenance acts. The substantial functionality of the trouble-shooting server 44 is communicating with the trouble-shooting client 40 at the service computer via the WLAN 46 and, together with the latter, to implement the function of remote monitoring. Furthermore, the trouble-shooting server 44 can also implement the remote request progression via an appropriate input by an operator of the imaging system 1, 2, 3, 4, at regular intervals following the end of a preset number of operating hours of the imaging system 1, 2, 3, 4, if a technical interference is detected via a monitoring parameter of the imaging system 1, 2, 3, 4, or as an outcome of the operating status.

After the process has been initiated either by the trouble-shooting client 42, or by the trouble-shooting server 44, the trouble-shooting server 44 transmits maintenance data to the trouble-shooting client 42, which at least characterize the imaging system 1, 2, 3, 4, and the device configuration for maintenance purposes. The trouble-shooting client 42 uses these maintenance data to determine the service documentation matching the respective imaging system 1, 2, 3, 4. In addition, the trouble-shooting server 44 can transmit information regarding the operational status, which provides clues as to whether the imaging system 1, 2, 3, 4 is operating normally or with interference. Furthermore, the operating status information can also contain a clue as to whether the imaging system 1, 2, 3, 4 is operating, or idling, or has even been switched off.

As a function of the received maintenance data, the trouble-shooting client 42 accesses the respectively suitable service documentation and determines a suitable starting point for a check routine on the basis of the operational status information received. The check routine for the respective imaging system 1, 2, 3, 4 is documented or contained in the service documentation. The check routine represents a routine check of customary or other maintenance acts, such as the renewal of wear- or consumable materials, re-calibration of device settings, read-out of protocol data sets, or checks regarding the interference-free functioning of device components. Moreover, the check routine can process predetermined error searching algorithms which, at the occurrence of a determined operational interference or a technical problem, are used to troubleshoot or determine the respective cause of the problem. These error searching algorithms can advantageously be configured as error searching tree structures wherein information regarding the operational status or a monitoring parameter is requested at each branching.

Based on the respectively activated check routine, or based on a reached point within the check routine, the trouble-shooting client 42 determines which monitoring parameter or which operational status information is needed for continuing the check routine. Via the WLAN, other network or communications connection, the trouble-shooting client 42 directs or forwards an appropriate request to the trouble-shooting server 44. The trouble-shooting server 44 determines the respective information and transmits the information to the trouble-shooting client 42 via the WLAN. The trouble-shooting client 42 evaluates the received information within the framework of the check routine and arrives at the next point in the check routine at which an input value is needed from the monitoring imaging system 1, 2, 3, 4. The trouble-shooting client 42 then directs a query corresponding to this input value to the trouble-shooting server 44 via the WLAN. The trouble-shooting server 44 determines the input value at the imaging system 1, 2, 3, 4 and transmits the input value in turn to the trouble-shooting client 42 via the WLAN. The interactive interrogation of operational status information and monitoring parameters is performed until the service software has processed the entire check routine or reached an end-point. From this process or algorithm, which was interactively processed via the WLAN, the reason for a problem may be identified in the form of an interference with the operation of the imaging system 1, 2, 3, 4, or a maintenance act to be performed by the service technician. Thereupon, the service web pad 40 displays information regarding the cause of the problem or the pending maintenance act.

The service technician can use the displayed information for planning his further work schedule. For example, prior to visiting the imaging system 1, 2, 3, 4 to be serviced, the service technician may obtain or collect consumable materials, for example coolant or a system battery, to take along tailored or appropriate tools needed for maintenance purposes, to obtain information regarding the peculiarities of maintenance acts, or to bring along a second person. This precautionary planning of a maintenance act may makes the work of the service technician more efficient in that the service technician does not have to visit in person the respective imaging system 1, 2, 3, 4 first for planning maintenance acts.

The above described progression is suited for the use of in-house service technicians entrusted with the regular maintenance of a plurality of devices, but who do not have highly specialized knowledge of the devices. Such in-house service technicians can themselves perform maintenance acts at a first service level with the aid of the service documentation, as well as the service software in the web pad 40, and are aided in efficient operations. Other more or less experienced technicians may use the progression.

However, one outcome of the check routine is a graver, more complex or profound reason for a problem or a maintenance act. The in-house service technician may not be able to address the problem or maintenance because of a lack of specialized knowledge of the field. Thus, if following the processing of the check routine and the taking of appropriate acts, the status of the imaging system 1, 2, 3, 4 is not in order, identified in the drawing figure by an "ok?" check 48. As a reaction, a service ticket 50 is activated, which, within the framework of a higher service level, is directed to a central service provider or to the manufacturer of the device. The service ticket 50 can be either manually activated by the in-house service technician, or the trouble-shooting client 42 in the web pad 40 of the in-house technician activates the service ticket 50 automatically.

Figure 2:
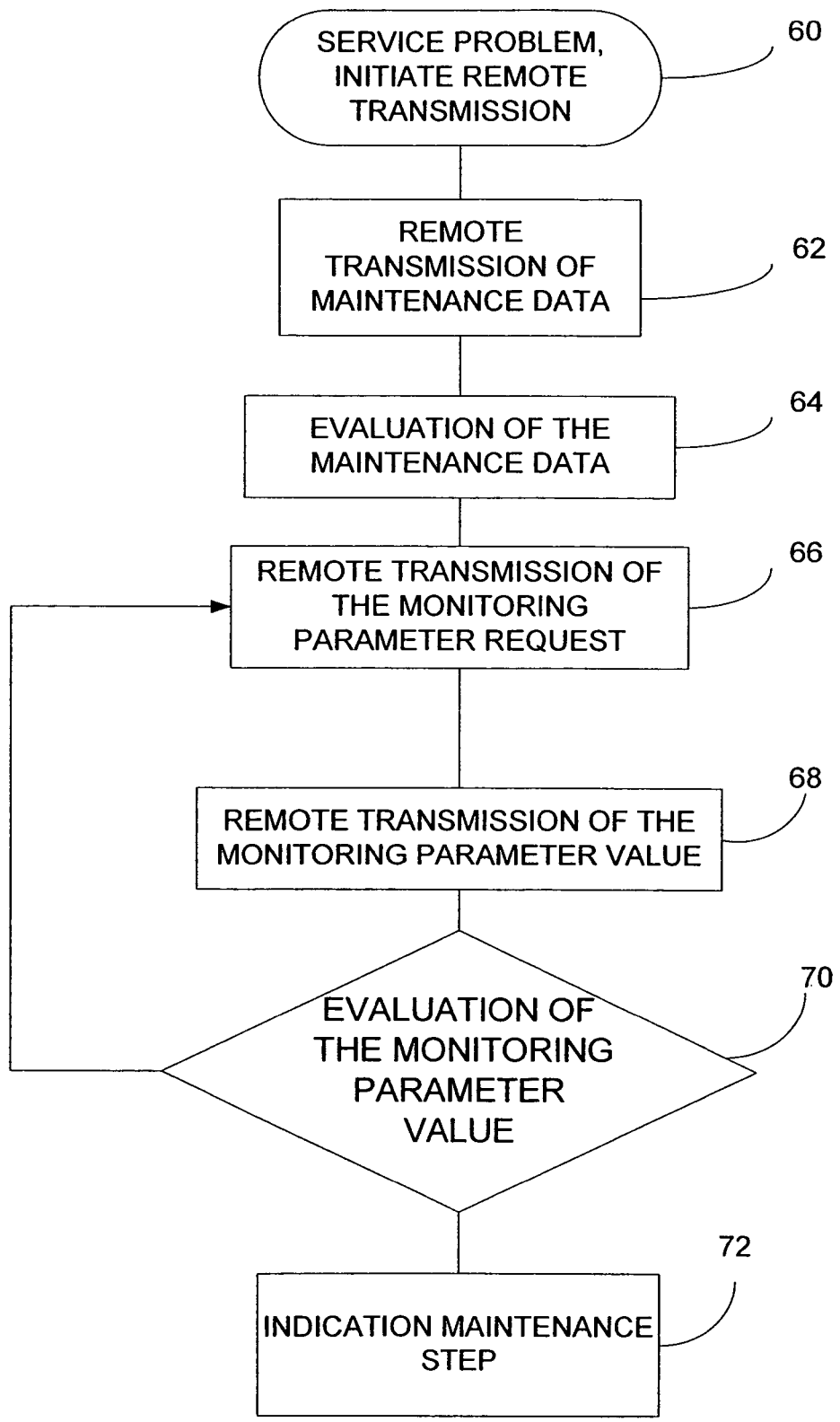
FIG. 2 is a flow chart of an embodiment of a method for a remote check.

The interactive processing of the check routine via the WLAN is represented in a schematic of the flow chart in FIG. 2. A service problem to be overcome appears in a first act 60 and leads to the initiation of a remote transmission between the service computer 40 and the device to be serviced. The service problem originates from the progression of a pre-defined number of operating hours or from the appearance of a technical interruption or a technical problem.

In a second act 62 following initialization, the process of remote transmission of maintenance data follows. The maintenance data are transmitted from the device to be serviced to the service computer 40 and include at least an identification of the device to be serviced which is sufficient for maintenance purposes and possibly the device configuration. In addition, information regarding the operational status of the device, for example whether used at the time or whether operating free of interference, is transmitted.

In a further act 64, the evaluation of the maintenance data by the service computer 40 takes place. Based on the maintenance data, the service computer 40 determines which service documentation to address and which check routine to process from which starting point. The service computer 40 determines which information to acquire from the device to be serviced as the input value for the further processing of the check routine.

In a further act 66, a monitoring parameter request is transmitted by the service computer 40 to the device to be serviced. The request specifies those values which desired by the service software.

The requested value is picked up or detected at the device to be serviced in a further act 68 and is remotely transmitted to the service computer 40. Detection of the value can originate from an interrogation of the actual monitoring parameter value via a sensor installation which, for example, can detect a device component temperature, a coolant level, a coolant temperature, a CPU temperature or an aging parameter of an X-ray tube. In addition, monitoring parameter values may be determined by mining or seeking sensor data which had been previously recorded or by reading out the contents of protocol devices, for example protocol data sets.

An evaluation of the received monitoring parameter value takes place in a further act 70 on the part of the service computer 40 via the service software. From this evaluation, a further point in the progression of the check routine is reached. For example, a further branching in an error search tree structure whose processing needs the determination of a further input value from the device to be serviced is reached. In a processing loop, a monitoring parameter request is again remotely transmitted in act 66. However, the evaluation may indicate that a check routine is completely processed and an outcome of this check routine is available.

In a final act 72, the display of the maintenance information which is pending for the checked or investigated device is generated. This indication takes place at an optical or acoustic display device and provides information to the service technician who, via his service computer 40, can utilize information obtained via the above described process for planning his work schedule. Thus, prior to visiting the device to be serviced, the technician can obtain consumable materials or software updates, information regarding device values to be set or calibrated, or a second person for the maintenance work.

Figure 3:
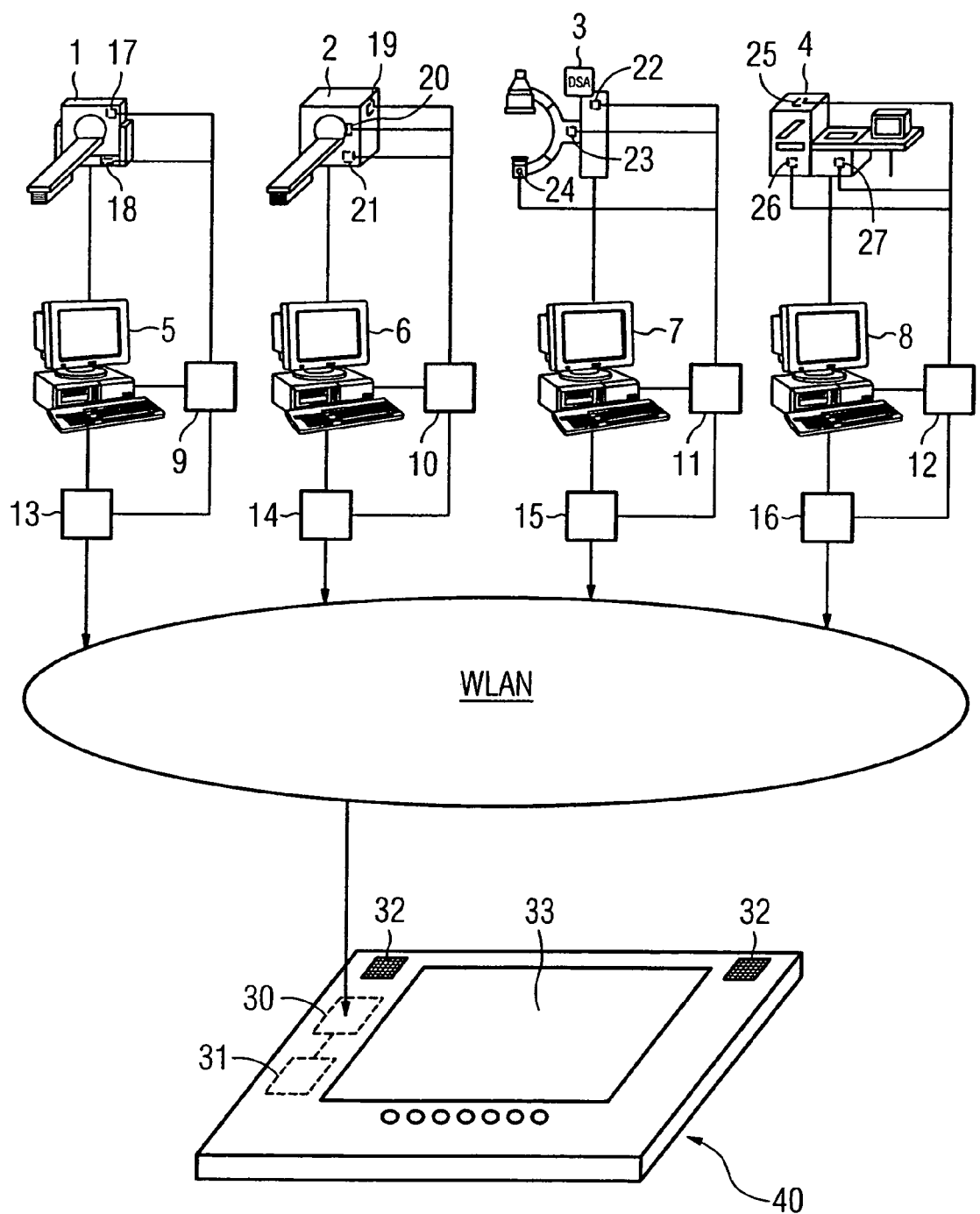
FIG. 3 is the schematic structure of one embodiment of an apparatus system in a hospital environment.

A hospital system, making use of the above described process, is schematically represented in FIG. 3. The system is comprised of a plurality of imaging systems 1, 2, 3, 4, which had been expanded by software and/or hardware modules for implementing the above described process.

A CT device 1 with an associated workstation computer 5 is represented. The workstation computer 5 is connected with a maintenance module 9. The workstation computer 5 and the maintenance module 9 can access a remote transmission module 13 which is suitable for the wireless data transmission in a local network WLAN. The maintenance module 9 has access to a network voltage sensor 18 which monitors a network voltage for operating the CT device 1. A collapse of the network voltage can lead to interference with the service, image data errors and even to the outage of the CT device 1. The maintenance module 9 is furthermore connected or coupled with a temperature sensor 17 which measures the temperature of the X-ray image detection unit of the CT device 1. Temperature fluctuations at this location can lead to substantial losses in a quality of the image data.

An MR device 2 connects with a workstation computer 6. A maintenance module 10 is connected with the workstation computer 6, both of which can access a WLAN remote transmission module 14. The maintenance module 10 contains data from a protocol arrangement 21 of the MR device. The data includes predetermined reports and events of the operation, for example examination times, interference reports, information regarding network voltage fluctuations, times for switch-on and switch-off, software or hardware error reports, an available memory location, or the states of peripheral output devices, for example printers.

The maintenance module 10 moreover has access to a coolant sensor 19 which measures the coolant level for cooling the superconducting magnetic coils, and a coil position sensor 20 which measures the positions of magnetic coils which are to be variably positioned.

A C-arc device 3 connects with an associated workstation computer 7. A maintenance module 11 is connected with the workstation computer 7, both of which have access to a WLAN remote transmission module 15. The maintenance module 11 has access to a position sensor 22 which detects a position of the adjustable C-arc, to a displacement motor sensor 23 which measures the activities of the displacement motor for adjusting the C-arc 3, and to an X-ray tube aging sensor 24 which generates a measured value in respect to the aging of the X-ray tube on the basis of the connection between the X-ray voltage, the X-ray current and the radiation doses.

A laboratory analysis device 4 performs chemical analyses in a controlled manner. The laboratory analysis device 4 is connected with an associated workplace computer 8. The workplace computer 8 is connected with a maintenance module 12, both of which have access to a WLAN remote transmission module 16. The maintenance module 12 receives sensor data from a heating lamp sensor 25 which checks the functioning of a heating lamp in the laboratory analysis device 4, from a coolant sensor 26 which checks the coolant level of the cooling device of a reaction chamber of the laboratory analysis device 4, and from a protocol arrangement 27 which protocols reports and operational states of the device.

Thus, each one of the above mentioned sensors is used for the detection of monitoring parameters from a respectively associated monitoring or maintenance module. If a monitoring parameter is predetermined by a monitoring parameter request, the respective sensor is thereby identified unequivocally. The maintenance modules 9, 10, 11, 12 are connected via the WLAN remote transmission modules 13, 14, 15, 16 with the web pad 40 of a service technician. The web pad 40 has an integrated remote transmission module 30 which is WLAN-capable. The web pad 40 has an integrated remote transmission module 31 which can be installed as a hardware component can be inserted, or is recorded as a software component in the web pad 40. The remote control transmission module 31 is capable of implementing the process described in connection with FIGS. 1 and 2 by interacting with the maintenance modules 9, 10, 11, 12. The remote control transmission module 31 employs appropriate service software which has also been recorded on the web pad 40 and which has access to a service documentation also recorded there. The service documentation includes information regarding check routines, error search tree structures, device settings and maintenance acts for the devices 1, 2, 3, 4 to be remotely monitored via the web pad 40.

Moreover, the web pad 40 has an acoustic indicator device, represented by a loudspeaker 32, and an optical indicator device, represented by a display screen 33. Pending maintenance acts, device settings for maintenance acts, information regarding consumable materials, and/or information regarding service tickets can be displayed on the display screen 33. The service technician is enabled via this information to plan his own maintenance work, and/or to monitor maintenance acts which he has directed per service tickets to a central maintenance provider or the respective manufacturer of the device. In addition there is the option of acoustically indicating predetermined urgent maintenance work, for example, for preventing or repairing cases of interference, via the loudspeaker 32 in order to compel the attention of the service technician, who might possibly be otherwise engaged at the time.

The invention claimed is:

1. A method for maintaining a device via a remote service computer, the method comprising the acts of:

transmitting maintenance data from the device to the service computer;
   automatically selecting a check routine based on the maintenance data, the check routine being used to troubleshoot or determine a cause of a problem in the device;
   evaluating the maintenance data received from the device within a framework of the check routine and arriving at a point in the check routine in which a monitoring parameter is needed;
   transmitting a request for the monitoring parameter needed in the check routine to the device as a function of the evaluation of the maintenance data;
   transmitting a parameter value of the monitoring parameter from the device to the service computer;
   evaluating the monitoring parameter value to determine whether another monitoring parameter is needed in the check routine from the device or the check routine is completed; and;
   transmitting a request for a subsequent monitoring parameter value from the service computer to the device based on the evaluation of the monitoring parameter value.

2. The method in accordance with claim 1, further comprising:
   initiating a transmission of the maintenance data with the device or the service computer; and
   displaying a result of the evaluation of the monitoring parameter value on the service computer.

3. The method in accordance with claim 1, wherein the transmission of the maintenance data from the device is initiated based on an input into the service computer by an operator.

4. The method in accordance with claim 1, wherein the device is configured to transmit the maintenance data at regular time intervals, on the basis of the monitoring parameter value reaching a predetermined threshold value and a combination thereof.

5. The method in accordance with claim 4, wherein the predetermined monitoring parameter value is detected by a sensor unit at the device and relates to one of a coolant temperature, an aging of an X-ray tube, a coolant level or a central processing unit (CPU) temperature.

6. The method in accordance with claim 4, wherein the predetermined monitoring parameter represents a report stored in a protocol data set of the device, the report being one of software or hardware error, an available memory location, or a status of peripheral output devices.

7. The method in accordance with claim 1, wherein the maintenance data transmitted from the device includes a device identification.

8. The method in accordance with claim 1, wherein the maintenance data includes an operational status of the device.

9. The method in accordance with claim 1, wherein the request for the monitoring parameter relates to a coolant temperature, an aging of an X-ray tube, a coolant level, a CPU temperature, a report stored in the protocol data set, or combinations thereof.

10. The method in accordance with claim 1, further comprising:
    outputting with an acoustic indicator device as a function of the evaluation.

11. The method in accordance with claim 10, wherein outputting comprises generating a sound as a function of a maintenance act pending in connection with the device.

12. The method in accordance with claim 11, wherein generating the sound comprises indicating an urgency of the maintenance act pending in connection with the device.

13. The method in accordance with claim 11, wherein outputting comprises outputting information regarding tools or consumable materials for the maintenance act pending in connection with the device, outputting information regarding work acts and device settings of the maintenance act pending in connection with the device, or combinations thereof.

14. The method in accordance with claim 1, further comprising:
outputting with an optical indicator device as a function of the evaluation.

15. The method in accordance with claim 14, wherein outputting comprises outputting information regarding a maintenance act pending in connection with the device.

16. The method in accordance with claim 15, wherein outputting the information comprises generating an optical indication related to an urgency of the maintenance act pending in connection with the device.

17. The method in accordance with claim 14, wherein outputting comprises outputting information regarding a position of the device.

18. The method in accordance with claim 15, wherein outputting comprises outputting information regarding tools or consumable materials for the maintenance act pending in connection with the device, outputting information regarding work acts and device settings of the maintenance act pending in connection with the device, or combinations thereof.

19. The method in accordance with claim 10, wherein outputting comprises outputting information regarding a position of the device.

20. The method in accordance with claim 1, wherein automatically selecting a check routine comprises automatically selecting a check routine starting point.

21. The method in accordance with claim 1, wherein transmitting the maintenance data comprises transmitting data identifying the device to be maintained and transmitting data including an operational status of the device to be maintained.

22. A system for maintaining a device via a remote service computer, the system comprising:
at least two sensor units operable to detect values of at least two monitoring parameters of the device;
a first maintenance module connected with the at least two sensor units;
a second maintenance module operable with the service computer; and
an indicator device operable with the service computer to display information from the service computer,
wherein the first maintenance module upon receiving data from the second maintenance module is configured to determine a monitoring parameter in response to a monitoring parameter request, to determine which one of the at least two sensor units is assigned to the monitoring parameter, to receive a monitoring parameter value from the assigned sensor, and to provide the monitoring parameter value to the second maintenance module,
wherein the monitoring parameter is needed in a check routine used to troubleshoot or determine a cause of a problem in the device and is stored in the service computer, and
wherein the second maintenance module is configured to automatically evaluate the monitoring parameter value to determine whether another monitoring parameter is needed in the check routine from the device and is configured to transmit a request for a subsequent monitoring parameter value to the first maintenance module based on the evaluation of the monitoring parameter value.

23. The system in accordance with claim 22 further comprising:
a first transmission module connected with the first maintenance module, the first transmission module operable to transmit maintenance data, the monitoring parameter value, or the maintenance data and the monitoring parameter value from the first maintenance module; and
a second transmission module connected with the second maintenance module, the second transmission module operable to receive data from the first transmission module.

24. The system in accordance with claim 22, wherein the first maintenance module is configured to transmit at regular time intervals, on the basis of the monitoring parameter values reaching corresponding predetermined threshold values, and combinations thereof.

25. The system in accordance with claim 22, wherein one of the at least two sensor units detects a coolant temperature, an aging of an X-ray tube, a coolant level, or a CPU temperature.

26. The system in accordance with claim 22, further comprising:
a protocol unit for recording reports regarding the operation of the device, the recorded reports being a software or hardware failure, an available memory location, status of peripheral output devices or combinations thereof.

27. The system in accordance with claim 22, wherein the second maintenance module is operable to evaluate automatically the monitoring parameter value received from the first maintenance module and to display an indication as a function of the evaluation of the received monitoring parameter value on or with the indicator device.

28. The system in accordance with claim 22, wherein the indicator device is an optical device.

29. The system in accordance with claim 22, wherein the indicator device is an acoustic device.

30. A method for maintaining a device via a remote service computer, the method comprising the acts of:
automatically selecting a check routine based on maintenance data received from a device, the check routine being used to troubleshoot or determine a cause of a problem in the device;
evaluating, by the remote service computer, the maintenance data within a framework of the check routine having a point in which a monitoring parameter is needed;
requesting, by the remote service computer, the monitoring parameter from the device as a function of the evaluation;
evaluating, by the remote service computer, a response, by the device, to the request for the monitoring parameter to determine whether another monitoring parameter is needed in the check routine or the check routine is completed; requesting by the remote service computer, the another monitoring parameter from the device as a function of the evaluation of the response; and
indicating a result of the evaluation of the response.

31. The method in accordance with claim 30, wherein the acts of evaluating comprise processing an error-search tree structure.

* * * * *